(12) United States Patent
Sang et al.

(10) Patent No.: US 10,544,079 B2
(45) Date of Patent: *Jan. 28, 2020

(54) PROCESS FOR THE DIRECT CONVERSION OF DIISOBUTENE TO A CARBOXYLIC ACID

(71) Applicant: EVONIK DEGUSSA GMBH, Essen (DE)

(72) Inventors: Rui Sang, Liaocheng (CN); Peter Kucmierczyk, Herne (DE); Kaiwu Dong, Bo Zhou (CN); Ralf Jackstell, Rostock (DE); Matthias Beller, Ostseebad Nienhagen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/189,029

(22) Filed: Nov. 13, 2018

(65) Prior Publication Data

US 2019/0194109 A1  Jun. 27, 2019

(30) Foreign Application Priority Data

Dec. 21, 2017 (EP) .................................. 17209336

(51) Int. Cl.
| | |
|---|---|
| *C07C 51/14* | (2006.01) |
| *B01J 31/18* | (2006.01) |
| *B01J 31/22* | (2006.01) |
| *B01J 31/24* | (2006.01) |
| *B01J 31/30* | (2006.01) |
| *C07C 53/126* | (2006.01) |

(52) U.S. Cl.
CPC .......... *C07C 51/14* (2013.01); *B01J 31/1815* (2013.01); *B01J 31/2208* (2013.01); *B01J 31/2295* (2013.01); *B01J 31/2404* (2013.01); *B01J 31/30* (2013.01); *B01J 2531/842* (2013.01); *C07C 53/126* (2013.01)

(58) Field of Classification Search
None
See application file for complete search history.

(56) References Cited

U.S. PATENT DOCUMENTS

| | | | | |
|---|---|---|---|---|
| 2,470,859 | A * | 5/1949 | Pavlic | C07C 51/235 562/531 |
| 3,641,074 | A | 2/1972 | Fenton | |
| 3,968,133 | A | 7/1976 | Knifton | |
| 2007/0282124 | A1* | 12/2007 | Eastham | B01J 31/0225 560/207 |
| 2018/0022773 | A1* | 1/2018 | Dong | C07C 67/38 556/144 |
| 2019/0194108 | A1* | 6/2019 | Sang | B01J 31/2234 |
| 2019/0194110 | A1* | 6/2019 | Sang | B01J 31/2234 |
| 2019/0194111 | A1* | 6/2019 | Sang | B01J 31/2295 |
| 2019/0194112 | A1* | 6/2019 | Sang | B01J 31/2234 |
| 2019/0194113 | A1* | 6/2019 | Sang | B01J 31/2234 |
| 2019/0194114 | A1* | 6/2019 | Sang | B01J 31/2234 |

FOREIGN PATENT DOCUMENTS

| | | |
|---|---|---|
| DE | 887644 C | 8/1953 |
| GB | 1595037 A | 8/1981 |
| WO | 2014/005854 A1 | 1/2014 |

OTHER PUBLICATIONS

U.S. Appl. No. 16/188,995, filed Nov. 13, 2018, Sang et al.
U.S. Appl. No. 16/215,991, filed Dec. 11, 2018, Sang et al.
U.S. Appl. No. 16/216,004, filed Dec. 11, 2018, Sang et al.
U.S. Appl. No. 16/216,020, filed Dec. 11, 2018, Sang et al.
U.S. Appl. No. 16/216,037, filed Dec. 11, 2018, Sang et al.
U.S. Appl. No. 16/216,053, filed Dec. 11, 2018, Sang et al.
European Search Report dated Jun. 21, 2018 in EP 17 20 9336 (5 pages).

* cited by examiner

*Primary Examiner* — Amy C Bonaparte
(74) *Attorney, Agent, or Firm* — Smith, Gambrell & Russell, LLP

(57) ABSTRACT

Process for the direct conversion of diisobutene to a carboxylic acid.

15 Claims, No Drawings

PROCESS FOR THE DIRECT CONVERSION OF DIISOBUTENE TO A CARBOXYLIC ACID

The invention relates to a process for the direct conversion of diisobutene to a carboxylic acid.

Carboxylic acids are used in the preparation of polymers, pharmaceuticals, solvents and food additives. The routes leading to carboxylic acids generally include the oxidation of hydrocarbons, alcohols or aldehydes, the oxidative cleavage of olefins by ozonolysis, the hydrolysis of triglycerides, nitriles, esters or amides, the carboxylation of Grignard or organolithium reagents, and the halogenation and subsequent hydrolysis of methyl ketones in the haloform reaction.

The object of the invention was to provide a process with which diisobutene (DIBN) can be directly converted to a carboxylic acid.

In the context of this application, "direct conversion" is intended to mean that the reaction takes place in one step, i.e. without separation or work-up or similar of an intermediate product.

This does not exclude, in the course of the reaction, intermediates forming which are directly converted onward.

The object is achieved by a process according to Claim 1.

Process comprising the process steps of:
a) addition of diisobutene;
b) addition of a complex, comprising a compound of general formula (I) and also Pd, or a compound according to general formula (I) and a substance comprising Pd

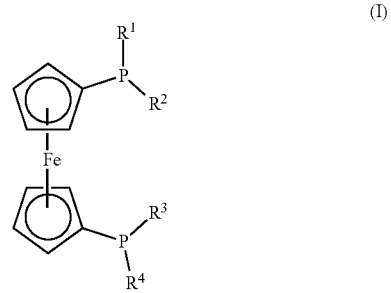

(I)

wherein $R^1$, $R^2$, $R^3$, $R^4$ are each independently selected from —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl;

at least one of the $R^1$, $R^2$, $R^3$, $R^4$ radicals is a —$(C_6-C_{20})$-heteroaryl radical having at least six ring atoms;

and $R^1$, $R^2$, $R^3$, $R^4$, if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl, may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—[$(C_1-C_{12})$-alkyl]$_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen;

c) feeding in CO;

d) heating the reaction mixture such that the diisobutene is converted to a carboxylic acid, wherein the diisobutene is directly converted to the carboxylic acid.

In a variant of the process, at least two of the $R^1$, $R^2$, $R^3$, $R^4$ radicals are a —$(C_6-C_{20})$-heteroaryl radical having at least six ring atoms.

In a variant of the process, the $R^1$ and $R^3$ radicals are each a —$(C_6-C_{20})$-heteroaryl radical having at least six ring atoms, In a variant of the process, the $R^1$ and $R^3$ radicals are each a —$(C_6-C_{20})$-heteroaryl radical having at least six ring atoms;

$R^2$ is —$(C_6-C_{20})$-heteroaryl having at least six ring atoms or is selected from —$(C_1-C_{12})$-alkyl, —$(C_3-C_{12})$-cycloalkyl, —$(C_3-C_{12})$-heterocycloalkyl, —$(C_6-C_{20})$-aryl;

and $R^4$ is selected from —$(C_1-C_{12})$-alkyl, —$(C_3-C_{12})$-cycloalkyl, —$(C_3-C_{12})$-heterocycloalkyl, —$(C_8-C_{20})$-aryl.

In a variant of the process, the $R^1$ and $R^3$ radicals are each a —$(C_6-C_{20})$-heteroaryl radical having at least six ring atoms.

and $R^2$ and $R^4$ are selected from —$(C_1-C_{12})$-alkyl, —$(C_3-C_{12})$-cycloalkyl, —$(C_3-C_{12})$-heterocycloalkyl, —$(C_6-C_{20})$-aryl.

In a variant of the process, the $R^1$ and $R^3$ radicals are each a —$(C_6-C_{20})$-heteroaryl radical having at least six ring atoms;

and $R^2$ and $R^4$ are —$(C_1-C_{12})$-alkyl.

In a variant of the process, $R^1$, $R^2$, $R^3$, $R^4$, if they are a heteroaryl radical, are each independently selected from pyridyl, pyridazinyl, pyrimidyl, pyrazinyl, benzofuranyl, indolyl, isoindolyl, benzimidazolyl, quinolyl, isoquinolyl.

In a variant of the process, the compound (I) has the structure (1):

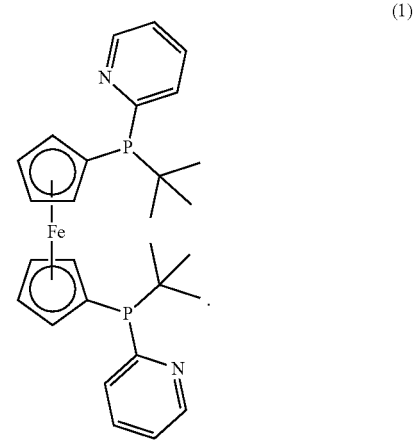

(1)

In a variant of the process, the substance in process step b) is selected from: PdCl$_2$, PdBr$_2$, Pd(acac)$_2$, Pd(dba)$_2$ (dba=dibenzylideneacetone), PdCl$_2$(CH$_3$CN)$_2$.

In a variant of the process, the substance in process step b) is Pd(acac)$_2$.

In a variant of the process, the process comprises the additional process step e) e) addition of acetic acid.

In a variant of the process, the process comprises the additional process step f) f) addition of water.

In a variant of the process, the process comprises the additional process step g) g) addition of p-toluenesulfonic acid (PTSA).

In a variant of the process, the reaction mixture is heated to a temperature in the range from 80° C. to 160° C. in process step d).

In a preferred variant of the process, the reaction mixture is heated to a temperature in the range from 100° C. to 140° C. in process step d).

In a variant of the process, the CO is fed in in process step c) such that the reaction proceeds under a CO pressure in the range from 20 bar to 60 bar.

In a preferred variant of the process, the CO is fed in in process step c) such that the reaction proceeds under a CO pressure in the range from 30 bar to 50 bar.

In a variant of the process, the diisobutene is converted to the compound P1:

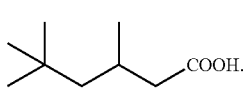

(P1)

The invention is elucidated in more detail by means of a working example below.

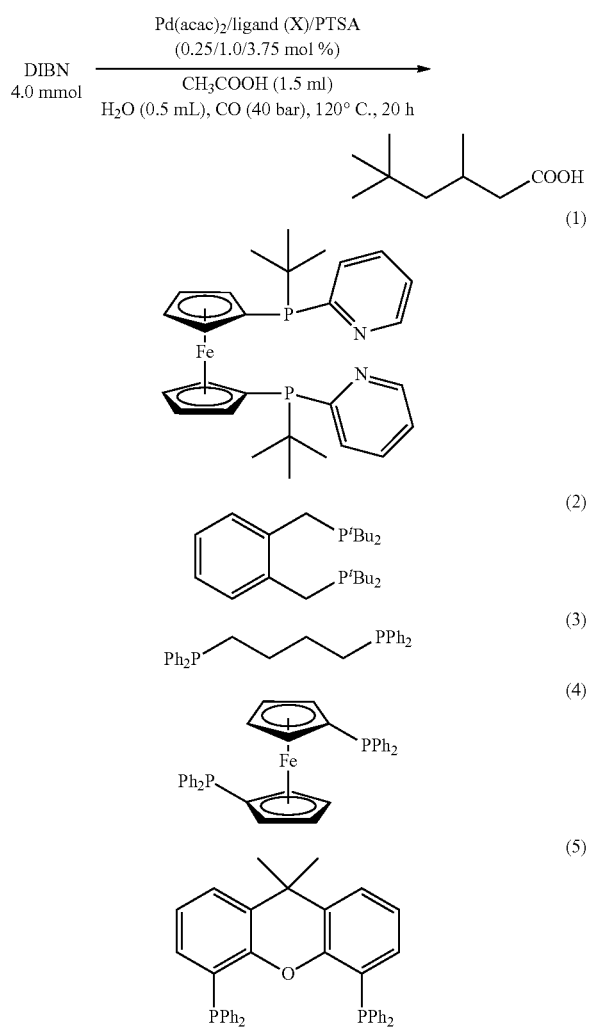

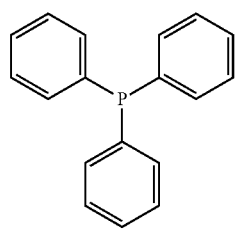

(6)

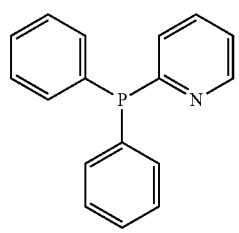

(7)

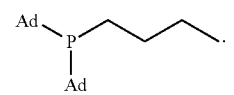

(8)

A 4 ml vial was charged with [Pd(acac)$_2$] (3.05 mg, 0.25 mol %), ligand (X) (20.64 mg, 1.0 mol %), p-toluenesulfonic acid (28.5 mg, 3.75 mol %) and an oven-dried stirrer bar. The vial was then sealed with septa (PTFE-coated styrene-butadiene rubber) and a phenol resin cap. The vial was evacuated and refilled with argon three times. H$_2$O (0.5 ml), acetic acid (1.5 ml) and diisobutene (DIBN) (4.0 mmol) were added to the vial with a syringe. The vial was placed in an alloy plate, which was transferred to an autoclave (300 ml) of the 4560 series from Parr Instruments under argon atmosphere. After flushing the autoclave three times with CO, the pressure of CO was increased to 40 bar at room temperature. The reaction was conducted at 120° C. for 20 h. On conclusion of the reaction, the autoclave was cooled down to room temperature and cautiously decompressed. Isooctane (100 µl) was then added as internal standard. Conversion was measured by GC analysis.

The above-described experiment was carried out with variation of the ligand (X), with X=1 to 8.

The results are compiled in the following table.

| Ligand | Yield (%) |
| --- | --- |
| (1)* | >99 |
| (2) | 7 |
| (3) | 39 |
| (4) | 26 |
| (5) | 16 |
| (6) | 8 |
| (7) | 13 |
| (8) | 29 |

*inventive process

As the experimental results show, the object is achieved by a process according to the invention.

The invention claimed is:

1. A process for preparing a carboxylic acid comprising:
   adding diisobutene,
   adding a complex, comprising a compound of general formula (I) and also Pd,
   or a compound according to general formula (I) and a substance comprising Pd

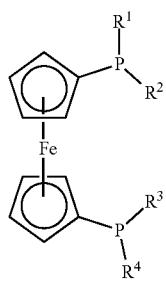

(I)

wherein
R¹, R², R³, R⁴ are each independently selected from —(C₁-C₁₂)-alkyl, —(C₃-C₁₂)-cycloalkyl, —(C₃-C₁₂)-heterocycloalkyl, —(C₆-C₂₀)-aryl or —(C₃-C₂₀)-heteroaryl; wherein
at least one of the R¹, R², R³, R⁴ radicals is a —(C₆-C₂₀)-heteroaryl radical having at least six ring atoms;
and
R¹, R², R³, and R⁴ are optionally substituted by one or more substituents selected from —(C₁-C₁₂)-alkyl, —(C₃-C₁₂)-cycloalkyl, —(C₃-C₁₂)-heterocycloalkyl, —O—(C₁-C₁₂)-alkyl, —O—(C₁-C₁₂)-alkyl-(C₆-C₂₀)-aryl, —O—(C₃-C₁₂)-cycloalkyl, —S—(C₁-C₁₂)-alkyl, —S—(C₃-C₁₂)-cycloalkyl, —COO—(C₁-C₁₂)-alkyl, —COO—(C₃-C₁₂)-cycloalkyl, —CONH—(C₁-C₁₂)-alkyl, —CONH—(C₃-C₁₂)-cycloalkyl, —CO—(C₁-C₁₂)-alkyl, —CO—(C₃-C₁₂)-cycloalkyl, —N—[(C₁-C₁₂)-alkyl]₂, —(C₆-C₂₀)-aryl, —(C₆-C₂₀)-aryl-(C₁-C₂)-alkyl, —(C₆-C₂₀)-aryl-O—(C₁-C₁₂)-alkyl, —(C₃-C₂₀)-heteroaryl, —(C₃-C₂₀)-heteroaryl-(C₁-C₁₂)-alkyl, —(C₃-C₂₀)-heteroaryl-O—(C₁-C₁₂)-alkyl, —COOH, —OH, —SO₃H, —NH₂ or halogen;
feeding in CO;
heating the reaction mixture such that the diisobutene is directly converted to the carboxylic acid.

2. The process according to claim 1,
wherein at least two of the R¹, R², R³, R⁴ radicals are a —(C₆-C₂₀)-heteroaryl radical having at least six ring atoms.

3. The process according to claim 1,
wherein the R¹ and R³ radicals are each a —(C₆-C₂₀)-heteroaryl radical having at least ring atoms.

4. The process according to claim 1,
wherein the R¹ and R³ radicals are each a —(C₆-C₂₀)-heteroaryl radical having at least six ring atoms;
R² is —(C₆-C₂₀)-heteroaryl having at least six ring atoms or is selected from —(C₁-C₁₂)-alkyl, —(C₃-C₁₂)-cycloalkyl, —(C₃-C₁₂)-heterocycloalkyl or —(C₆-C₂₀)-aryl;
and R⁴ is selected from —(C₁-C₁₂)-alkyl, —(C₃-C₁₂)-cycloalkyl, —(C₃-C₁₂)-heterocycloalkyl or —(C₆-C₂₀)-aryl.

5. The process according to claim 1,
wherein the R¹ and R³ radicals are each a —(C₆-C₂₀)-heteroaryl radical having at least six ring atoms;
and R² and R⁴ are selected from —(C₁-C₁₂)-alkyl, —(C₃-C₁₂)-cycloalkyl, —(C₃-C₁₂)-heterocycloalkyl or —(C₆-C₂₀)-aryl.

6. The process according to claim 1,
wherein the R¹ and R³ radicals are each a —(C₆-C₂₀)-heteroaryl radical having at least six ring atoms;
and R² and R⁴ are —(C₁-C₁₂)-alkyl.

7. The process according to claim 1,
wherein R¹, R², R³, R⁴, are each independently selected from pyridyl, pyridazinyl, pyrimidyl, pyrazinyl, benzofuranyl, indolyl, isoindolyl, benzimidazolyl, quinolyl or isoquinolyl.

8. The process according to claim 1,
wherein the compound (I) has the structure (1):

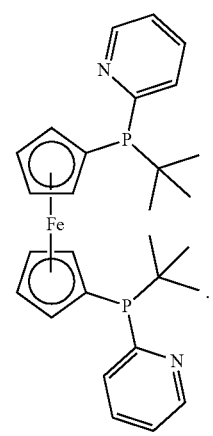

(1)

9. The process according to claim 1,
wherein the substance in process step b) is selected from:
PdCl₂, PdBr₂, Pd(acac)₂, Pd(dba)₂ (dba=dibenzylideneacetone) or PdCl₂(CH₃CN)₂.

10. The process according to claim 1,
wherein the process comprises
prior to heating the reaction mixture adding acetic acid.

11. The process according to claim 1,
wherein the process comprises
prior to heating the reaction mixture adding water.

12. The process according to claim 1,
wherein the process comprises
prior to heating the reaction mixture adding p-toluenesulfonic acid.

13. The process according to claim 1,
wherein the reaction mixture is heated to a temperature in the range from 80° C. to 160° C.

14. The process according to claim 1,
wherein the CO is fed in under pressure in the range from 20 bar to 60 bar.

15. The process according to claim 1,
wherein the diisobutene is converted to the compound P1:

(P1)

* * * * *